United States Patent [19]
Goodson, Jr. et al.

[11] Patent Number: 6,160,175
[45] Date of Patent: *Dec. 12, 2000

[54] NAPHTHYL ACETAMIDES AS SPLA$_2$ INHIBITORS

[75] Inventors: Theodore Goodson, Jr.; Richard W. Harper; David K. Herron, all of Indianapolis, Ind.

[73] Assignee: Eli Lilly and Company, Indianapolis, Ind.

[*] Notice: This patent issued on a continued prosecution application filed under 37 CFR 1.53(d), and is subject to the twenty year patent term provisions of 35 U.S.C. 154(a)(2).

[21] Appl. No.: 09/091,077

[22] PCT Filed: Dec. 9, 1996

[86] PCT No.: PCT/US96/19874

§ 371 Date: Jun. 9, 1998

§ 102(e) Date: Jun. 9, 1998

[87] PCT Pub. No.: WO97/21664

PCT Pub. Date: Jun. 19, 1997

Related U.S. Application Data

[60] Provisional application No. 60/008,558, Dec. 13, 1995.

[30] Foreign Application Priority Data

Feb. 5, 1996 [GB] United Kingdom .................. 9602267

[51] Int. Cl.$^7$ ................................................ C07C 233/00
[52] U.S. Cl. ........................ 564/172; 514/617; 562/466
[58] Field of Search ............................. 564/172; 514/617

[56] References Cited

FOREIGN PATENT DOCUMENTS

| | | |
|---|---|---|
| 71375/91 | 8/1991 | Austria . |
| 346788 | 12/1989 | European Pat. Off. . |
| 0 447285 | 9/1991 | European Pat. Off. . |

OTHER PUBLICATIONS

Chemical Abstracts, CA 55:22249b Caold.

J. Med. Chem. (1994), 37(5), 557–9 Coden: JMCMAR; Issn: 0022–2623.

Moszew, et al., Benzyl Derivatives of 1–Napthylacetic Acid as Plant Growth Regulators, Roczniki Chem. 1960, vol. 34, pp. 1387–1396.

*Primary Examiner*—Paul J. Killos
*Attorney, Agent, or Firm*—Arleen Palmberg

[57] ABSTRACT

A class of novel naphthyl acetamide compounds is disclosed together with the use of such compounds for inhibiting sPLA$_2$ mediated release of fatty acids for treatment of conditions such as septic shock.

11 Claims, No Drawings

NAPHTHYL ACETAMIDES AS SPLA$_2$ INHIBITORS

This application is a Continuation Prosecution Application of U.S. application Ser. No. 09/091,077 filed Jun. 9, 1998. This Appln is a International 371 of PCT/US96/19874 filed Dec. 9, 1996 and also claims the benefit of U.S. Provisional Appln Ser. No. 60/008,558 filed Dec. 13, 1995.

BACKGROUND OF THE INVENTION

This invention relates to novel naphthyl acetamides useful for inhibiting sPLA$_2$ mediated release of fatty acids for conditions such as septic shock.

The structure and physical properties of human non-pancreatic secretory phospholipase A$_2$ (hereinafter called, "sPLA$_2$") has been thoroughly described in two articles, namely, "Cloning and Recombinant Expression of Phospholipase A$_2$ Present in Rheumatoid Arthritic Synovial Fluid" by Seilhamer, Jeffrey J.; Pruzanski, Waldemar; Vadas Peter; Plant, Shelley; Miller, Judy A.; Kloss, Jean; and Johnson, Lorin K.; *The Journal of Biological Chemistry*, Vol. 264, No. 10, Issue of Apr. 5, 1989; pp. 5335–5338, and "Structure and Properties of a Human Non-pancreatic Phospholipase A$_2$" by Kramer, Ruth M.; Hession, Catherine; Johansen, Berit; Hayes, Gretchen; McGray, Paula; Chow, E. Pingchang; Tizard, Richard; and Pepinsky, R. Blake; *The Journal of Biological Chemistry*, Vol. 264, No. 10, Issue of Apr. 5, 1989; pp. 5768–5775, the disclosures of which are incorporated herein by reference.

It is believed that sPLA$_2$ is a rate limiting enzyme in the arachidonic acid cascade which hydrolyzes membrane phospholipids. Thus, it is important to develop compounds which inhibit sPLA$_2$ mediated release of fatty acids (e.g., arachidonic acid). Such compounds would be of value in general treatment of conditions induced and/or maintained by overproduction of sPLA$_2$, such as septic shock, adult respiratory distress syndrome, pancreatitis, trauma, bronchial asthma, allergic rhinitis, rheumatoid arthritis, and etc.

The Communication to the Editor by Hayden G. Beaton, et al., Journal of Medicinal Chemistry, 1994, Vols. 37, No. 5 describes various novel (naphthylthio) methyl analogs of nonphospholipid sPLA$_2$ inhibitors.

It is desireable to develop new compounds and treatments for sPLA$_2$ induced disesase.

This invention is a novel use of compounds known as naphthyl acetamide compounds of the formula I.

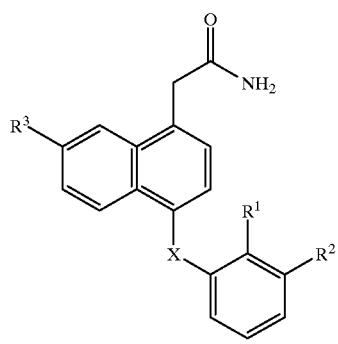

(I)

where $R^1$, $R^2$, $R^3$ and x are as hereinafter defined. These naphthyl acetamide compounds are effective in inhibiting human sPLA$_2$ mediated release of fatty acids.

This invention is also a novel class of naphthyl acetamide compounds having potent and selective effectiveness as inhibitors of human sPLA$_2$.

This invention is also a pharmaceutical composition containing a naphthyl acetamide compound.

This invention is also a method of preventing and treating septic shock, adult respiratory distress syndrome, pancreatitis, trauma, bronchial asthma, allergic rhinitis, rheumatoid arthritis, and related diseases by contact with a therapeutically effective amount of the naphthyl acetamide compounds of the invention.

Definitions:

The naphthyl acetamides of the invention employ certain defining terms as follows:

The term, "alkyl" by itself or as part of another substituent means, unless otherwise defined, a straight or branched chain monovalent hydrocarbon radical such as methyl, ethyl, n-propyl, isopropyl, n-butyl, tertiary butyl, isobutyl, sec-butyl, n-pentyl, and n-hexyl.

The term, "alkenyl" employed alone or in combination with other terms means a straight chain or branched monovalent hydrocarbon group having the stated number range of carbon atoms, and typified by groups such as vinyl, propenyl, crotonyl, isopentenyl, and various butenyl isomers.

The term, "alkynyl" employed alone or in combination with other terms means a straight or branched chain hydrocarbon having the stated number range of carbon atoms, and having a triple bond. The term includes groups such as acetylene, propyne, various butynl isomers and the like.

The term, "halo" means fluoro, chloro, bromo, or iodo.

The term, "non-interfering substituent", refers to radicals suitable for substitution at positions 2 or 3 of the phenyl ring. Illustrative non-interfering radicals are $C_1$–$C_6$ alkyl, $C_1$–$C_6$ alkenyl, $C_1$–$C_6$ alkynyl, $C_7$–$C_{12}$ aralkyl, $C_7$–$C_{12}$ alkaryl, $C_3$–$C_8$ cycloalkyl, $C_3$–$C_8$ cycloalkenyl, phenyl, toluyl, xylenyl, biphenyl, $C_1$–$C_6$ alkoxy, $C_1$–$C_6$ alkenyloxy, $C_1$–$C_6$ alkynyloxy, $C_2$–$C_{12}$ alkoxyalkyl, $C_2$–$C_{12}$ alkoxyalkyloxy, $C_2$–$C_{12}$ alkylcarbonyl, $C_2$–$C_{12}$ alkylcarbonylamino, $C_2$–$C_{12}$ alkoxyamino, $C_2$–$C_{12}$ alkoxyaminocarbonyl, $C_1$–$C_{12}$ alkylamino, $C_1$–$C_6$ alkylthio, $C_2$–$C_{12}$ alkyithiocarbonyl, $C_1$–$C_6$ alkylsulfinyl, $C_1$–$C_6$ alkylsulfonyl, $C_1$–$C_6$ haloalkoxy, $C_1$–$C_6$ haloalkylsulfonyl, $C_1$–$C_6$ haloalkyl, $C_1$–$C_6$ hydroxyalkyl, —C(O)O($C_1$–$C_6$ alkyl), —(CH$_2$)$_n$—O—($C_1$–$C_6$ alkyl), benzyloxy, phenoxy, phenylthio, —(CONHSO$_2$R), —CHO, amino, amidino, bromo, carbamyl, carboxyl, ethoxycarbonyl, —(CH$_2$)$_n$–CO$_2$H, chloro, cyano, cyanoguanidinyl, fluoro, guanidino, hydrazide, hydrazino, hydrazido, hydroxy, hydroxyamino, iodo, nitro, phosphono, —SO$_3$H, thioacetal, thiocarbonyl, and $C_1$–$C_6$ carbonyl; where n is from 1 to 8.

Compounds of the invention which are illustrative include the following:

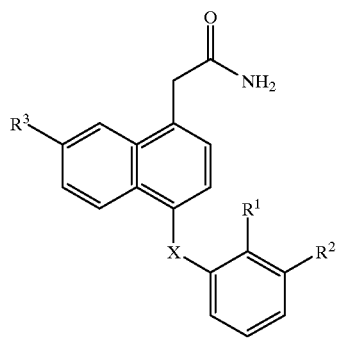

(I)

where:

R¹ and R² are each independently hydrogen or a non-interfering substituent with the proviso that at least one of R¹ or R² must be hydrogen;

R³ is hydrogen, —O(CH₂)$_n$Y,

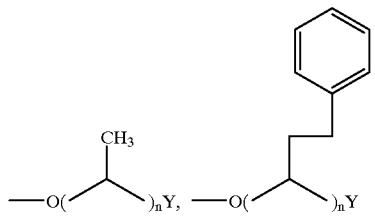

where n is a number from 2 to 4 and Y is —CO₂H, —PO₃H₂ or —SO₃H; and

X is —O— or —CH₂—.

A preferred subclass of compounds of formula I are those where R¹ and R² are each independently hydrogen or phenyl.

Another preferred subclass of compounds of formula I are those where R³ is —O(CH₂)$_n$Y, where n is 3 or 4 and Y is —CO₂H, —PO₃H₂ or —SO₃H.

Particularly preferred compounds of the invention are those where R¹ and R² are hydrogen and R³ is hydrogen or —O(CH₂)₃CO₂H.

Specific preferred compounds and all pharmaceutically acceptable salts, solvates and prodrug derivatives thereof which are illustrative of the compounds of the invention include the following:

Compound A

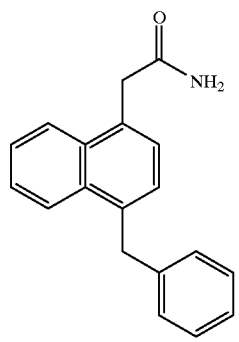

Compound B

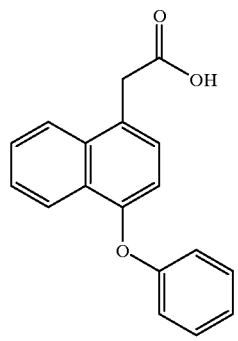

Compound C

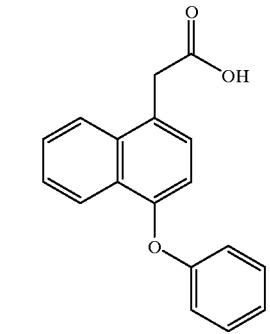

and mixtures of the above compounds in any combination.

The salts of the above naphthyl acetamides are an additional aspect of the invention. In those instances where the compounds of the invention possess acidic or basic functional groups various salts may be formed which are more water soluble and physiologically suitable than the parent compound. Representative pharmaceutically acceptable salts, include but are not limited to, the alkali and alkaline earth salts such as lithium, sodium, potassium, calcium, magnesium, aluminum and the like. Salts are conveniently prepared from the free acid by treating the acid in solution with a base or by exposing the acid to an ion exchange resin.

Included within the definition of pharmaceutically acceptable salts are the relatively non-toxic, inorganic and organic base addition salts of compounds of the present invention, for example, ammonium, quaternary ammonium, and amine cations, derived from nitrogenous bases of sufficient basicity to form salts with the compounds of this invention (see, for example, S. M. Berge, et al., "Pharmaceutical Salts," *J. Phar. Sci.*, 66: 1–19 (1977)). Moreover, the basic group(s) of the compound of the invention may be reacted with suitable organic or inorganic acids to form salts such as acetate, benzenesulfonate, benzoate, bicarbonate, bisulfate, bitartrate, borate, bromide, camsylate, carbonate, chloride, clavulanate, citrate, chloride, edetate, edisylate, estolate, esylate, fluoride, fumarate, gluceptate, gluconate, glutamate, glycolylarsanilate, hexylresorcinate, bromide, chloride, hydroxynaphthoate, iodide, isothionate, lactate, lactobionate, laurate, malate, malseate, mandelate, mesylate, methylbromide, methylnitrate, methylsulfate, mucate, napsylate, nitrate, oleate, oxalate, palmitate, pantothenate, phosphate, polygalacturonate, salicylate, stearate, subacetate, succinate, tannate, tartrate, tosylate, trifluoroacetate, trifluoromethane sulfonate, and valerate.

Synthesis Methods

Compounds where x is oxygen can be prepared by the following Scheme I.

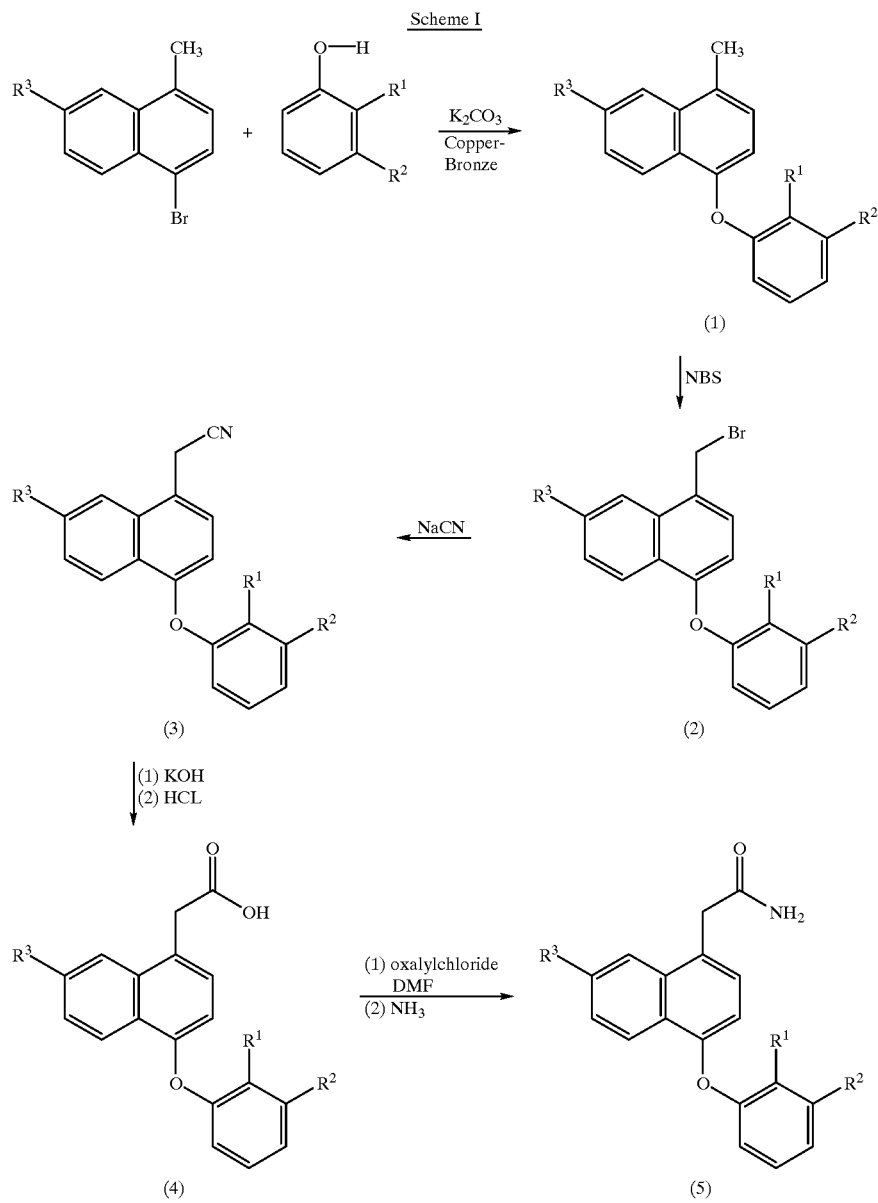

Scheme I

In the first step of the above reaction scheme, an appropriately substituted 1-bromo-4-methylnapthalene and an appropriately substituted phenol are dissolved in an aprotic polar solvent such as pyridine. The mixture is treated with an excess of potassium carbonate and an excess of copper-bronze and refluxed under a nitrogen blanket to produce (1).

Bromination of compound (1) to produce (2) is accomplished by refluxing (1) with a brominating agent, such as N-bromosuccinamide, in a non-polar alkyl halide solvent, such as carbon tetrachloride, using 2,2-azobisisobutyronitrile as a catalyst.

Treatment of (2) with sodium cyanide produces (3). This reaction is best conducted in an aprotic polar solvent, such as dimethyl sulfoxide (DMSO), while heating to a temperature of about 60° C.

Hydrolysis of the cyano compound (3) to produce the acid (4) is accomplished in two steps. Using a polar protic solvent, such as diethylene glycol as a cosolvent, the cyano compound (3) is treated with an alkali metal base, such as potassium hydroxide, and the mixture is heated to about 90–95° C. The resultant product is then reacted with a strong mineral acid such as hydrochloric acid.

Conversion of (4) to the desired naphthyl acetamide compound (5) is accomplished by another two-step process. First, the acid (4) is dissolved in an alkyl halide solvent such as methylene chloride. The acid/alkyl halide solution is chilled in an ice bath then treated with oxalyl chloride, using dimethylformamide (DMF) as a catalyst, to produce the acid chloride. The solution is allowed to warm to room temperature and then treated with ammonia gas at room temperature to produce (5).

The desired product (5) can be purified using standard recrystallization procedures in a suitable organic solvent, preferably methylene chloride/hexane.

Compounds where X is methylene can be prepared by the following Scheme II

Scheme II

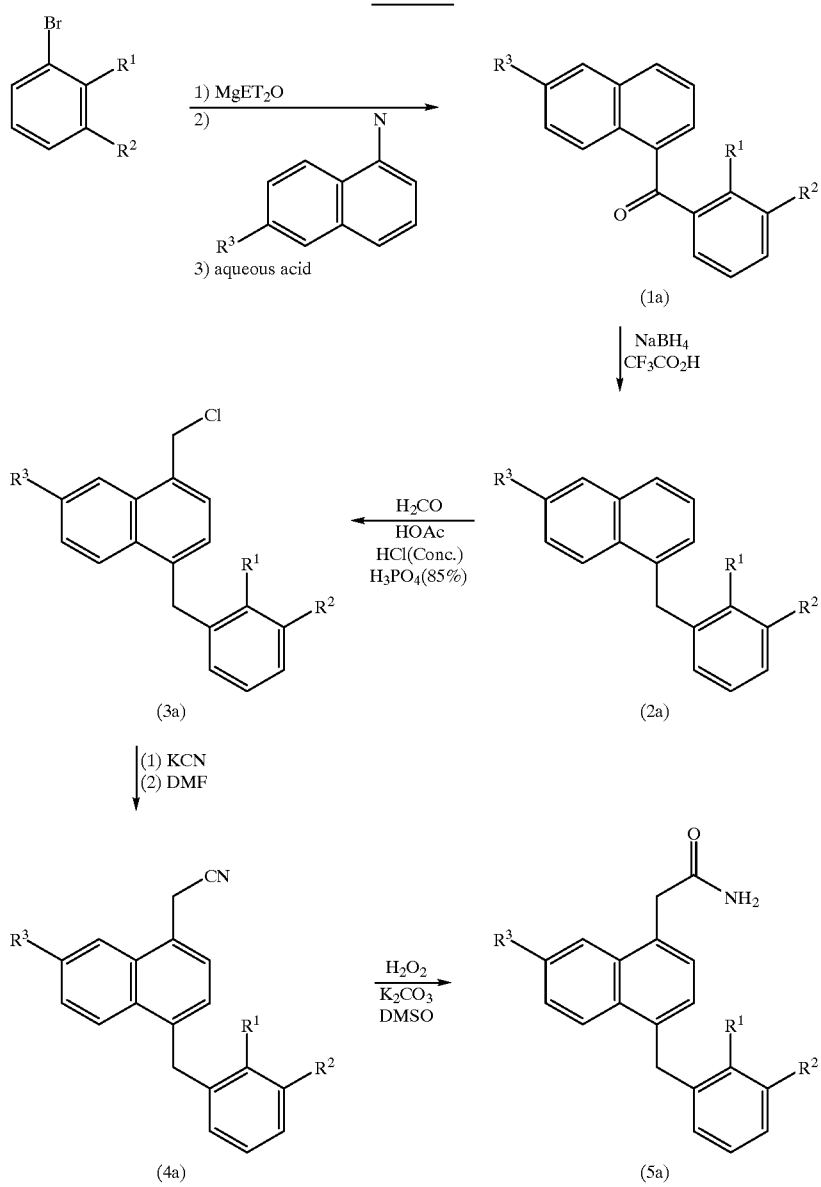

Compound (1a) is prepared by a grignard reaction. The Grignard reagent starting material is prepared by reacting an appropriately substituted phenyl bromide with magnesium and ether. The reagent is then reacted with an appropriately substituted naphthyl nitrile and the resultant compound is hydrolyzed with an aqueous acid such as hydrochloric acid to form the benzoyl napthyl (1a).

Reduction of (1a) is accomplished by treatment with a molar excess of a reducing agent such as sodium borohydride. The reaction is initiated in an ice bath using a solvent-catalyst such as trifluoroacetic acid and then allowed to warm to room temperature as the reduction proceeds.

Chloromethylation of (2a) is achieved by treatment with an excess of formaldehyde and concentrated hydrochloric acid in a polar acidic solvent such as an acetic/phosphoric acid mixture. The reaction is best conducted at a temperature of about 90° C.

The nitrile 4(a) is prepared by a nucleophilic displacement of the chloride compound (3a) with cyanide. The reaction is conducted by refluxing (3a) with a slight molar excess in an aprotic polar solvent of sodium cyanide such as dimethyl-formamide (DMF) for about five hours, then allowing the reaction to continues while it cools to room temperature.

The desired naphthylamide (5a) is then prepared from the nitrile (4a) in a three-step process. To a solution of nitrile (4a), dissolved in an aprotic polar solvent such as DMSO, potassium carbonate is added to make the nitrile solution slightly basic. Hydrolysis of the nitrile is then achieved by treatment with an aqueous hydrogen peroxide solution. Crystallization of the naphthyl acetamide may be accomplished by adding water to the peroxide solution.

Compounds where $R^3$ is other than hydrogen can be readily prepared by using a 1-bromo-4-methyl-napthalene with a protected phenol, such as a methoxy group, on the 6-position of the napthalene ring as a starting material. The process is conducted, as described above, to prepare compounds (1)–(3). Acid hydrolysis of the cyano group (3) and deprotection of the rotected phenol can be accomplished by treating (3) with a 40% hydrogen bromide solution in acetic acid. The deprotected phenol can then be reacted to prepare the appropriate substituent at the 6-position of the napthyl ring. For example, preparation of compounds where $R^3$ is —O(CH$_2$)$_n$COOH can be achieved by alkyalting the phenol with an appropriate alkyl halide followed by conversion to the acid by treatment with a base such as aqueous sodium hydroxide followed by dilute hydrochloric acid.

It will be readily appreciated by one skilled in the art that the substituted phenol and phenyl bromide starting materials are either commercially available or can be readily prepared by known techniques from commercially available starting materials. All other reactants and reagents used to prepare the compounds of the present invention are commercially available.

The following examples further illustrate the preparation of the compounds of this invention as well as the compounds used in the method of this invention. The examples are illustrative only and are not intended to limit the scope of the invention in any way.

EXAMPLE 1

Preparation of 4-Benzyl-1-naphphylacetamide (Compound A)

A. Preparation of 1-benzoylnaphthalene

To 10.3 g (65 mMol) of bromobenzene in 50 mL of diethyl ether, magnesium turnings were added. The reaction was initiated by adding a few crystals of iodine to about 5 mL of the bromobenzene solution, and warming gently. The remainder of the bromobenzene was then added at such a rate as to maintain a mild reflux. When the reaction had abated, 1-naphthonitrile was added slowly in 50 mL of diethyl ether. The mixture was allowed to stir at room temperature overnight. Water was added, and the mixture acidified to pH 1 with concentrated hydrochloric acid. Methylene chloride was added and the mixture was heated under reflux overnight. The layers were separated, and the organic layer was washed with brine and dried over magnesium sulfate. The subtitled product was crystallized from methylene chloride/hexane, then further purified by medium pressure column chromatography on silica gel, eluting with ethyl acetate:hexane/5:95. The desired product was obtained as a white crystalline solid (4.38 g; 29% yield).

M.P.=72–74° C. Elemental Analysis: Calculated: C, 87.91; H, 5.21. Found: C, 87.99; H, 5.36.

B. Preparation of 1-benzylnaphthalene

Sodium hydride pellets (98% NaH; 3.5 g; 5.3 eq) were added to 50 mL of trifluoroacetic acid at ice-water bath temperature, under nitrogen atmosphere. 1-Benzoylnaphthalene (4.0 g; 17.2 mMol), as prepared above, in 25 mL of methylene chloride, was added dropwise. The mixture was allowed to stir overnight while warming to room temperature. The mixture was poured onto ice, the layers were separated, and the aqueous layer was extracted with methylene chloride. The combined organic extractions were washed with saturated sodium bicarbonate, and brine; then dried over magnesium sulfate, and concentrated under reduced pressure. The residue was subjected to medium pressure chromatography on silica gel, eluting with ethyl acetate:hexane/5:95. The desired product was obtained as a white powder (3.0 g; 80% yield).

Mass spec. (m/z): 218. M.P. 57–59° C. Elemental Analysis for C$_{17}$H$_1$: Calculated: C, 93.54; H, 6.46. Found: C, 93.81; H, 6.65.

C. Preparation of 1-benzyl-2-chloromethylnaphthalene

1-Benzylnaphthalene (3.0 g; 13.7 mMol), as prepared above, formaldehyde (1.0 g; 35.7 mMol), glacial acetic acid (4.3 g; 71.7 mMol), concentrated hydrochloric acid (6.5 mL) and 85% phosphoric acid (4.3 mL) were combined and heated in an oil bath maintained at 90° C. for 4.5 hr. The reaction mixture was cooled, a small amount of water was added, and extraction was carried out with diethyl ether. The combined organic extractions were washed with sodium carbonate (10% aqueous), and brine; then dried over magnesium sulfate. The solvent was removed under reduced pressure, and the residue subjected to medium pressure chromatography on silica gel eluting with hexane. The product (1.18 g; 32% yield) was isolated as a colorless oil which subsequently crystallized.

Mass spec. (m/z): 266. Elemental Analysis for C$_{18}$H$_{15}$C$_1$: Calculated: C, 81.04; H, 5.67. Found: C, 81.24; H, 5.70.

D. 4-benzyl-1-cyanomethnaphthalene 1-benzyl-2-chloromethylnaphthalene (1.14 g; 4.3 mMol) was combined with potassium cyanide (0.35 g; 1.2 eq) in dimethyl formamide (DMF, 40 mL) and allowed to stir at room temperature for three days. The mixture was poured into ice-water and allowed to stir for two hours. Extraction was carried out with ethyl acetate. The combined organic extractions were washed with brine and dried over magnesium sulfate. The solvent was removed under reduced pressure, and the residue subjected to medium pressure chromatography on silica gel eluting with ethyl acetate:hexane/10:90. The subtitled product was obtained as a white crystalline solid (0.23 g; 21% yield).

Mass spec. (m/z): 257. M.P. 124–128° C. Elemental Analysis for C$_{19}$H$_{15}$N: Calculated C, 88.68; H, 5.88; N, 5.44. Found C, 88.47; H, 6.12; N, 5.41.

E. Preparation of 4-benzyl-1-naphphylacetamide

4-Benzyl-1-cyanomethylnaphthalene (0.19 g; 0.7 mMol), as prepared above, potassium carbonate (0.2 g; 1.4 mMol) and 30% hydrogen peroxide (0.5 mL) were combined in 3.0 mL of dimethyl sulfoxide (DMSO) and allowed to stir at room temperature for one hour. Water was added and the title product was isolated by filtration as a white crystalline solid (92 mg; 45% yield).

Mass spec. (m/z): 275. M.P. 157–159° C. Elemental analysis for C$_{19}$H$_{17}$NO: Calculated C, 82.88; H, 6.22; N, 5.09. Found C, 82.86; H, 6.30; N, 4.98.

EXAMPLE 2

Preparation of 4-Phenoxynaphth-1-yl acetic acid (Compound B)

A. Preparation of 1-methyl-4-phenoxynaphthalene

To a 3-neck flask fitted with a mechanical stirrer, 600 mL of pyridine (dried over molecular sieve), 100 g of 4-bromo-1-methylnaphthalene, 55.6 g of phenol, 83.7 g of potassium carbonate, 14.9 g of copper(I)chloride, and 2 g copper bronze was added. Under a nitrogen atmosphere, the mixture was refluxed for 72 hours with vigorous stirring. The reaction mixture was cooled and poured into cold dilute hydrochloric acid, and the resulting mixture was extracted with ethyl acetate. The organic layer was washed two times with cold dilute hydrochloric acid, dried over sodium sulfate, and filtered. After removing the solvent under vacuum, the product was flash chromatographed over silica gel with hexane elution. The product was further purified through fractional distillation, obtaining 35 g (33%) of the desired 1-methyl-4-phenoxynaphthalene intermediate at 150° C. at 0.075 torr.

Elemental Analysis for C$_{17}$H$_{14}$O: Calculated: C, 87.15; H, 6.02. Found: C, 87.13; H, 6.11.

B. Preparation of 1-bromomethyl-4-phenoxynaphthalene

To 200 mL of carbon tetrachloride, 20 g of the phenoxynaphthalene prepared above, 15.2 g of N-bromosuccinimide, and 100 mg of freshly distilled 2,2-azobisisobutyronitrile was added. The reaction mixture was heated and maintained at reflux with mechanical stirring for 16 hours. The reaction mixture was cooled, and the precipitated succinimide was filtered off. After removing solvent under vacuum, the product was redissolved in hexane and filtered. On removing solvent again, 17.2 g (72%) of 1-bromomethyl-4-phenoxynaphthalene, as an oil, was obtained, which was used subsequently without further purification. A small sample was applied to a preparative silica gel plate and eluted with 1:1 ethyl acetate to hexane to provide for characterization.

Elemental Analysis for $C_{17}H_{13}BrO$: Calculated: C, 65.20; H, 4.18. Found: C, 64.92; H, 4.21.

C. Preparation of 1-cyanomethyl-4-phenoxynaphthalene

Sodium cyanide (3.7 g; 75 mMol) was dissolved in DMSO (50 mL, dried over molecular sieves). The mixture was heated in an oil bath maintained at 50° C., and 15.7 g (50 mMol) of 1-bromomethyl-4-phenoxynaphthalene, prepared as described above, in 75 mL of DMSO was added dropwise. After addition was complete, stirring was continued for 0.5 hours. The temperature was raised to 70° C., and stirring was continued for 1.0 hour. The oil bath was turned off, and the stirring was continued overnight. The mixture was poured onto ice, and extracted with ether. The combined organic extractions were washed with brine and dried over magnesium sulfate. The product was obtained as a white, crystalline solid (6.24 g; 49% yield). mass 259. A sample was purified for analysis by medium pressure chromatography on silica gel, eluting with ethyl acetate:hexane/1:9.

Elemental Analysis for $C_{18}H_{13}NO$: Calculated C, 83.37; H, 5.05; N, 5.40. Found C, 83.32; H, 5.17; N, 5.27.

D. Preparation of 4-phenoxynaphthalene-1-yl-acetic acid

Into 25 mL of diethylene glycol, 500 mg of the above cyanomethyl intermediate was dissolved. After adding 1 g of potassium hydroxide dissolved in 10 mL water, the mixture was stirred and heated at 85–90° C. for 16 hours. The reaction mixture was cooled and poured into cold dilute hydrochloric acid. The mixture was extracted with ethyl acetate, and the organic layer was washed two times with brine. The organic layer was shaken with dilute potassium carbonate, and the resulting aqueous layer was separated, acidified with dilute hydrochloric acid, and extracted with ethyl acetate. The organic layer was dried over magnesium sulfate, filtered, and evaporated under vacuum, giving 300 mg (56%) of 4-phenyoxynaphth-1-yl acetic acid as an amorphous solid, which was used without further purification.

Mass spec. (m/z): 278 NMR (CDCl3) δ (ppm/TMS): 4.1(s,2H), 6.9(d,$_1$H), 7.1(d,2H), 7.2(t,1H), 7.3–7.4(M,3H), 7.5(t,1H), 7.6(t,1H), 8.0(d,1H), 8.3(d,1H).

EXAMPLE 3

Preparation of 4-Phenoxynaphth-1-yl acetamide (Compound C)

Into 20 mL of methylene chloride, 0.250 g of the naphthyl acetic acid prepared as in Example 2 above, was dissolved. After cooling the solution in an ice bath, 0.090 mL of oxalyl chloride and a few drops of dimethylformamide were added. After 30 minutes, the ice bath was removed, and the reaction was allowed to come to room temperature over 30 minutes. The solvent of the reaction mixture was removed under vacuum, and product was redissolved in 50 mL of methylene chloride, followed by evaporation under vacuum, giving the napthylacetyl chloride as an oil. This product was redissolved in 40 mL of methylene chloride, and excess ammonia was bubbled in over 15 minutes at room temperature. After stirring overnight, the solvent of the reaction mixture was removed under vacuum. The reaction product was redissolved in ethyl acetate and washed with brine and dilute potassium carbonate. The organic solution was dried over sodium sulfate, and filtered. The solvent was removed under vacuum, and the product was redissolved in a minimum of methylene chloride. On dilution to cloudiness with hexane and after cooling, 130 mg (55%) of 4-phenoxynaphth-1-yl-acetamide was obtained.

M.P.=119–22° C. Analysis for $C_{18}H_{15}NO_2$: Calculated: C, 77.96; H, 5.45; N, 5.05. Found: C, 76.99; H, 5.38; N, 4.66.

Therapeutic Use of Naphthyl Acetamide Compounds

The naphthyl acetamide compounds described herein are believed to achieve their beneficial therapeutic action principally by direct inhibition of human $sPLA_2$, and not by acting as antagonists for arachidonic acid, nor other active agents below arachidonic acid in the arachidonic acid cascade, such as 5-lipoxygenases, cyclooxygenases, and etc.

The method of the invention for inhibiting $sPLA_2$ mediated release of fatty acids comprises contacting $sPLA_2$ with an therapeutically effective amount of naphthyl acetamide compound its salt or a prodrug derivative thereof.

The specific dose of a compound administered according to this invention to obtain therapeutic or prophylactic effects will, of course, be determined by the particular circumstances surrounding the case, including, for example, the compound administered, the route of administration and the condition being treated. Typical daily doses will contain a non-toxic dosage level of from about 0.01 mg/kg to about 50 mg/kg of body weight of an active compound of this invention.

The compounds of the invention may be used in a method of treating a mammal (e.g., a human) to alleviate the pathological effects of septic shock, adult respiratory distress syndrome, pancreatitus, trauma, bronchial asthma, allergic rhinitis, and rheumatoid arthritis; wherein the method comprises administrating to the mammal naphthyl acetamide compound represented by formulae (I) in a therapeutically effective amount. A therapeutically effective amount is an amount sufficient to inhibit $sPLA_2$ mediated release of fatty acid and to thereby inhibit or prevent the arachidonic acid cascade and its deleterious products. The therapeutic amount of compound of the invention needed to inhibit $sPLA_2$ may be readily determined by taking a sample of body fluid and assaying it for $SPLA_2$ content by conventional methods.

Pharmaceutical Formulations of the Invention

As previously noted the compounds of this invention are useful for inhibiting $sPLA_2$ mediated release of fatty acids such as arachidonic acid. By the term, "inhibiting" is meant the prevention or therapeutically significant reduction in release of $sPLA_2$ initiated fatty acids by the compounds of the invention. By "pharmaceutically acceptable" it is meant the carrier, diluent or excipient must be compatible with the other ingredients of the formulation and not deleterious to the recipient thereof.

Preferably the pharmaceutical formulation is in unit dosage form. The unit dosage form can be a capsule or tablet itself, or the appropriate number of any of these. The quantity of active ingredient in a unit dose of composition may be varied or adjusted from about 0.1 to about 1000 milligrams or more according to the particular treatment involved. It may be appreciated that it may be necessary to make routine variations to the dosage depending on the age and condition of the patient. The dosage will also depend on the route of administration.

The compound can be administered by a variety of routes including oral, aerosol, rectal, transdermal, subcutaneous, intravenous, intramuscular, and intranasal.

Pharmaceutical formulations of the invention are prepared by combining (e.g., mixing) a therapeutically effective amount of the naphthyl acetamide compounds of the invention together with a pharmaceutically acceptable carrier or diluent therefor. The present pharmaceutical formulations are prepared by known procedures using well known and readily available ingredients.

In making the compositions of the present invention, the active ingredient will usually be admixed with a carrier, or diluted by a carrier, or enclosed within a carrier which may be in the form of a capsule, sachet, paper or other container. When the carrier serves as a diluent, it may be a solid, semi-solid or liquid material which acts as a vehicle, or can be in the form of tablets, pills, powders, lozenges, elixirs, suspensions, emulsions, solutions, syrups, aerosols (as a solid or in a liquid medium), or ointment, containing, for example, up to 10% by weight of the active compound. The compounds of the present invention are preferably formulated prior to administration.

For the pharmaceutical formulations any suitable carrier known in the art can be used. In such a formulation, the carrier may be a solid, liquid, or mixture of a solid and a liquid. Solid form formulations include powders, tablets and capsules. A solid carrier can be one or more substances which may also act as flavoring agents, lubricants, solubilisers, suspending agents, binders, tablet disintegrating agents and encapsulating material.

Tablets for oral administration may contain suitable excipients such as calcium carbonate, sodium carbonate, lactose, calcium phosphate, together with disintegrating agents, such as maize, starch, or alginic acid, and/or binding agents, for example, gelatin or acacia, and lubricating agents such as magnesium stearate, stearic acid, or talc.

In powders the carrier is a finely divided solid which is in admixture with the finely divided active ingredient. In tablets the active ingredient is mixed with a carrier having the necessary binding properties in suitable proportions and compacted in the shape and size desired. The powders and tablets preferably contain from about 1 to about 99 weight percent of the active ingredient which is the novel compound of this invention. Suitable solid carriers are magnesium carbonate, magnesium stearate, talc, sugar lactose, pectin, dextrin, starch, gelatin, tragacanth, methyl cellulose, sodium carboxymethyl cellulose, low melting waxes, and cocoa butter.

Sterile liquid form formulations include suspensions, emulsions, syrups and elixirs.

The active ingredient can be dissolved or suspended in a pharmaceutically acceptable carrier, such as sterile water, sterile organic solvent or a mixture of both. The active ingredient can often be dissolved in a suitable organic solvent, for instance aqueous propylene glycol. Other compositions can be made by dispersing the finely divided active ingredient in aqueous starch or sodium carboxymethyl cellulose solution or in a suitable oil.

The following pharmaceutical formulations 1 through 8 are illustrative only and are not intended to limit the scope of the invention in any way. "Active ingredient", refers to a compound according to Formula (I) or a pharmaceutically acceptable salt, solvate, or prodrug thereof.

Formulation 1

Hard gelatin capsules are prepared using the following ingredients:

|  | Quantity (mg/capsule) |
| --- | --- |
| Active ingredient | 250 |
| Starch, dried | 200 |
| Magnesium stearate | 10 |
| Total | 460 mg |

Formulation 2

A tablet is prepared using the ingredients below:

|  | Quantity (mg/tablet) |
| --- | --- |
| Active ingredient | 250 |
| Cellulose, microcrystalline | 400 |
| Silicon dioxide, fumed | 10 |
| Stearic acid | 5 |
| Total | 665 mg |

The components are blended and compressed to form tablets each weighing 665 mg

Formulation 3

An aerosol solution is prepared containing the following components:

|  | Weight |
| --- | --- |
| Active ingredient | 0.25 |
| Ethanol | 25.75 |
| Propellant 22 (Chlorodifluoromethane) | 74.00 |
| Total | 100.00 |

The active compound is mixed with ethanol and the mixture added to a portion of the propellant 22, cooled to −30° C. and transferred to a filling device. The required amount is then fed to a stainless steel container and diluted with the remainder of the propellant. The valve units are then fitted to the container.

Formulation 4

Tablets, each containing 60 mg of active ingredient, are made as follows:

| | |
|---|---|
| Active ingredient | 60 mg |
| Starch | 45 mg |
| Microcrystalline cellulose | 35 mg |
| Polyvinylpyrrolidone (as 10% solution in water) | 4 mg |
| Sodium carboxymethyl starch | 4.5 mg |
| Magnesium stearate | 0.5 mg |
| Talc | 1 mg |
| Total | 150 mg |

The active ingredient, starch and cellulose are passed through a No. 45 mesh U.S. sieve and mixed thoroughly. The aqueous solution containing polyvinylpyrrolidone is mixed with the resultant powder, and the mixture then is passed through a No. 14 mesh U.S. sieve. The granules so produced are dried at 50° C. and passed through a No. 18 mesh U.S. sieve. The sodium carboxymethyl starch, magnesium stearate and talc, previously passed through a No. 60 mesh U.S. sieve, are then added to the granules which, after mixing, are compressed on a tablet machine to yield tablets each weighing 150 mg.

Formulation 5

Capsules, each containing 80 mg of active ingredient, are made as follows:

| | |
|---|---|
| Active ingredient | 80 mg |
| Starch | 59 mg |
| Microcrystalline cellulose | 59 mg |
| Magnesium stearate | 2 mg |
| Total | 200 mg |

The active ingredient, cellulose, starch, and magnesium stearate are blended, passed through a No. 45 mesh U.S. sieve, and filled into hard gelatin capsules in 200 mg quantities.

Formulation 6

Suppositories, each containing 225 mg of active ingredient, are made as follows:

| | |
|---|---|
| Active ingredient | 225 mg |
| Saturated fatty acid glycerides | 2,000 mg |
| Total | 2,225 mg |

The active ingredient is passed through a No. 60 mesh U.S. sieve and suspended in the saturated fatty acid glycerides previously melted using the minimum heat necessary. The mixture is then poured into a suppository mold of nominal 2 g capacity and allowed to cool.

Formulation 7

Suspensions, each containing 50 mg of active ingredient per 5 ml dose, are made as follows:

| | |
|---|---|
| Active ingredient | 50 mg |
| Sodium carboxymethyl cellulose | 50 mg |
| Syrup | 1.25 ml |
| Benzoic acid solution | 0.10 ml |
| Flavor | q.v. |
| Color | q.v. |
| Purified water to total | 5 ml |

The active ingredient is passed through a No. 45 mesh U.S. sieve and mixed with the sodium carboxymethyl cellulose and syrup to form a smooth paste. The benzoic acid solution, flavor and color are diluted with a portion of the water and added, with stirring. Sufficient water is then added to produce the required volume.

Formulation 8

An intravenous formulation may be prepared as follows:

| | |
|---|---|
| Active ingredient | 100 mg |
| Isotonic saline | 1,000 ml |

The solution of the above ingredients generally is administered intravenously to a subject at a rate of 1 ml per minute.

Assay Experiments

Chromogenic Assay

The following chromogenic assay procedure was used to identify and evaluate inhibitors of recombinant human secreted phospholipase $A_2$. The assay described herein has been adapted for high volume screening using 96 well microtiter plates. A general description of this assay method is found in the article, "Analysis of Human Synovial Fluid Phospholipase $A_2$ on Short Chain Phosphatidylcholine-Mixed Micelles: Development of a Spectrophotometric Assay Suitable for a Microtiterplate Reader", by Laure J. Reynolds, Lori L. Hughes, and Edward A. Dennis, Analytical Biochemistry, 204, pp. 190–197, 1992 (the disclosure of which is incorporated herein by reference):
Reagents:

| | |
|---|---|
| REACTION BUFFER - | |
| $CaCl_2.2H_2O$ | (1.47 g/L) |
| KCl | (7.455 g/L) |
| Bovine Serum Albumin (fatty acid free) | (1 g/L) |
| (Sigma A-7030, product of Sigma Chemical Co. St. Louis MO, USA) | |
| TRIS HCl | (3.94 g/L) |
| pH 7.5 (adjust with NaOH) | |
| ENZYME BUFFER - | |
| 0.05 $NaOAc.3H_2O$, pH 4.5 | |
| 0.2 NaCl | |
| Adjust pH to 4.5 with acetic acid | |
| DTNB - 5,5'-dithiobis-2-nitrobenzoic acid | |
| RACEMIC DIHEPTANOYL THIO - PC | |
| racemic 1,2-bis (heptanoylthio)-1,2-dideoxy-sn-glycero-3-phosphorylcholine | |
| TRITON X-100 ™ prepare at 6.249 mg/ml in reaction buffer to equal 10 uM. | |
| REACTION MIXTURE - | |

A measured volume of racemic dipheptanoyl thio PC supplied in chloroform at a concentration of 100 mg/ml is taken to dryness and redissolved in 10 millimolar TRITON X-100™ nonionic detergent aqueous solution. Reaction Buffer is added to the solution, then DTNB to give the Reaction Mixture.

The reaction mixture thus obtained contains 1 mM diheptanoly thio-PC substrate, 0.29 mm Triton X-100™ detergent, and 0.12 mm DTMB in a buffered aqueous solution at pH 7.5.

Assay Procedure:

1. Add 0.2 ml reaction mixture to all wells;

2. Add 10 ul test compound (or solvent blank) to appropriate wells, mix 20 seconds;

3. Add 50 nanograms of sPLA$_2$ (10 microliters) to appropriate wells;

4. Incubate plate at 40° C. for 30 minutes;

5. Read absorbance of wells at 405 nanometers with an automatic plate reader.

All compounds were tested in triplicate. Typically, compounds were tested at a final concentration of 5 ug/ml. Compounds were considered active when they exhibited 40% inhibition or greater compared to uninhibited control reactions when measured at 405 nanometers. Lack of color development at 405 nanometers evidenced inhibition. Compounds initially found to be active were reassayed to confirm their activity and, if sufficiently active, IC$_{50}$ values were determined. Typically, the IC$_{50}$ values (see, Table I, below) were determined by diluting test compound serially two-fold such that the final concentration in the reaction ranged from 45 ug/mL to 0.35 ug/ml. More potent inhibitors required significantly greater dilution. In all cases, % inhibition measured at 405 nanometers generated by enzyme reactions containing inhibitors relative to the uninhibited control reactions was determined. Each sample was titrated in triplicate and result values were averaged for plotting and calculation of IC$_{50}$ values. IC$_{50}$ were determined by plotting log concentration versus inhibition values in the range from 10–90% inhibition.

TABLE I

Results of Human Secreted Phospholipase A$_2$ Inhibition Tests

| Compound of Example number | Inhibition of human secreted PLA$_2$ μM IC$_{50}$ ± mean deviation (3–4 tests) |
|---|---|
| 1. Compound A | 0.87 |
| 2. Compound B | 51 |
| 3. Compound C | 4.4 |

While the present invention has been illustrated above by certain specific embodiments, it is not intended that these embodiments should limit the scope of the invention as described in the appended claims.

We claim:

1. A naphthyl acetamide compound or a pharmaceutically acceptable salt, solvate or prodrug derivative thereof; wherein said compound is represented by the formula I

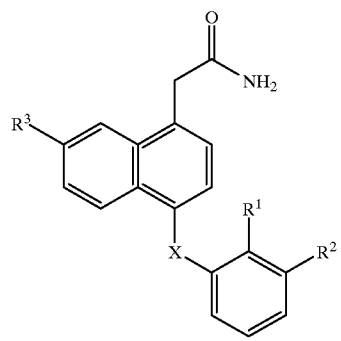

wherein
R$^1$ and R$^2$ are each independently hydrogen or a non-interfering substituent with the proviso that at least one of R$^1$ and R$^2$ must be hydrogen;
R$^3$ is . . . , —O(CH$_2$)$_n$Y,

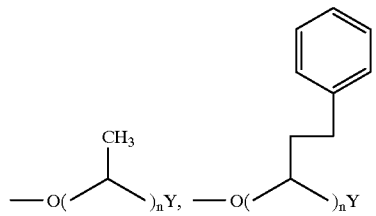

where n is from 2 to 4 and Y is —CO$_2$H, —PO$_3$H$_2$ or SO$_3$H; and
X is —O— or —CH$_2$.

2. The compound of formula I as claimed in claim 1 wherein R$^1$ and R$^2$ are each independently hydrogen or phenyl and R$^3$ is . . . , —O(CH$_2$)$_n$Y, where n is from 2 to 4 and Y is —CO$_2$H, —PO$_3$H$_2$ or SO$_3$H.

3. The compound of formula I as claimed in claim 1 which is

Compound A

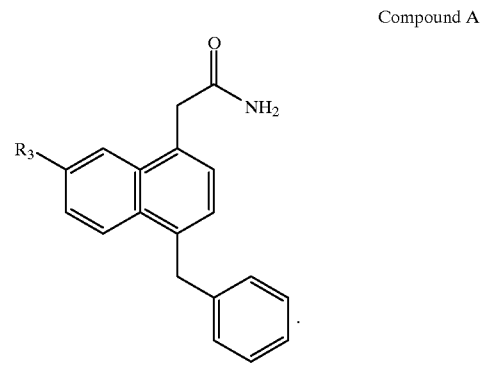

4. A pharmaceutical formulation comprising a naphthyl acetamide compound of formula I as claimed in any one of claims 1 to 3 together with a pharmaceutically acceptable carrier or diluent therefor.

5. A method of treating a mammal to alleviate the pathological effects of septic shock, adult respiratory distress syndrome, pancreatitis, trauma, bronchial asthma, allergic rhinitis, and rheumatoid arthritis; wherein the method comprises administration to said mammal a naphthyl acetamide compound as claimed in any one of claims 1 to 3 in an amount sufficient to inhibit sPLA$_2$ mediated release of fatty acid and to thereby inhibit or prevent the arachidonic acid cascade and its deleterious products.

6. A method of inhibiting sPLA$_2$ mediated release of fatty acids in humans comprising administering a therapeutically effective amount of a compound fomula II

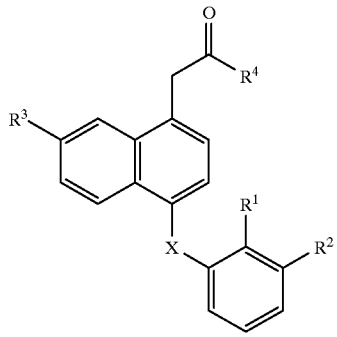

(II)

Wherein

R$^1$ and R$^2$ are each independently hydrogen or a non-interfering substituent with the proviso that at least one of R$^1$ and R$^2$ must be hydrogen;

R$^3$ is a hydrogen, —O(CH$_2$)nY,

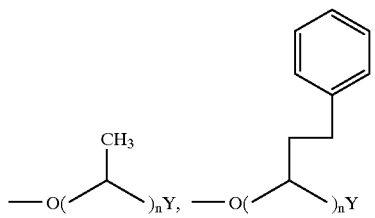

where n is from 2 to 4 and Y is —CO$_2$H, —PO$_3$H$_2$ or —SO$_3$H; R$^4$ is —NH$_2$, or —OH; and X is —O— or —CH$_2$—.

7. A method of claim 6 wherein R$^1$ and R$^2$ are eah independently hydrogen or phenyl;

R$^3$ is hydrogen or —O(CH$_2$)nY, where n is from 2 to 4 and Y is —CO$_2$H, —PO$_3$H$_2$ or —SO$_3$H$_3$; and R$^4$ is —NH$_2$ or —OH.

8. A method of claim 7 wherein the compounds is

Compound A

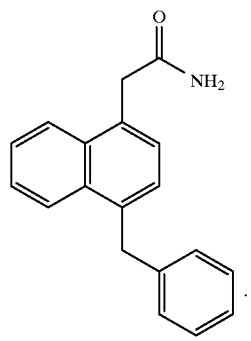

9. A metod of selectively inhibiting sPLA$_2$ mediated release of fatty acids in humans comprising administering therapeutically effective amount of a compound of formula II

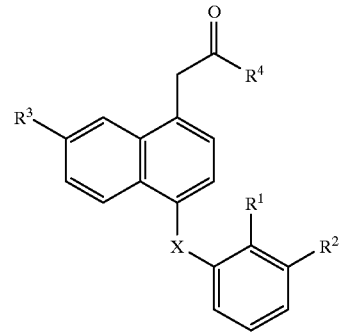

(II)

Wherein

R$^1$ and R$^2$ are each independently hydrogen or a non-interfering substituent with the proviso that at least one of R$^1$ and R$^2$ must be hydrogen; R$^3$ is hydrogen, —O(Chd 2)nY,

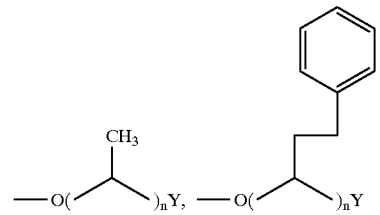

wherein n is from 2 to 4 and Y is —CO$_2$H, —PO$_3$H or —SO$_3$H; R$^4$ is —NH$_2$, or —OH; and X is —O— or —CH$_2$.

10. A method of claim 9 wherein R$^1$ and R$^2$ are each independently hydrogen or phenyl;

R$^3$ is hydrogen or —O(CH$_2$)nY where n is from 2 to 4 and Y is —CO$_2$H, —PO$_3$H$_2$ or —SO$_3$H$_3$; and R$^4$ is —NH$_2$ or —OH.

11. A method of claim 10, wherein the compound is

Compound A

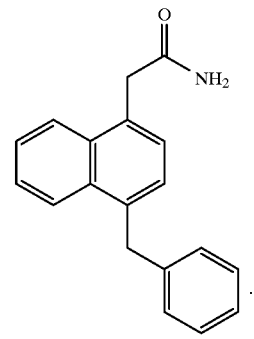

* * * * *